United States Patent
Tricca et al.

[11] Patent Number: 5,338,538
[45] Date of Patent: Aug. 16, 1994

[54] PREBRUSHING PYROPHOSPHATE-CONTAINING LIQUID ORAL COMPOSITIONS

[75] Inventors: Robert E. Tricca, Redwood City, Calif.; William T. Doran, Dover; Catherine L. Gray, Morristown, both of N.J.

[73] Assignee: Pfizer Inc, New York, N.Y.

[21] Appl. No.: 80,023

[22] Filed: Jun. 18, 1993

Related U.S. Application Data

[63] Continuation-in-part of Ser. No. 896,275, Jun. 10, 1992, abandoned, which is a continuation-in-part of Ser. No. 736,851, Jul. 29, 1991, abandoned.

[51] Int. Cl.$^5$ ............................................. A61K 7/16
[52] U.S. Cl. .................................... 424/57; 424/49
[58] Field of Search ................................. 424/49-58

[56] References Cited

U.S. PATENT DOCUMENTS

| | | | |
|---|---|---|---|
| 2,054,742 | 9/1936 | Elbel | 167/93 |
| 3,004,897 | 10/1961 | Shore | 167/93 |
| 43,822,599 | 4/1989 | Mitra | 424/52 |
| 4,081,526 | 3/1978 | Asakawa et al. | 424/57 |
| 4,150,151 | 4/1979 | Pader et al. | 424/56 |
| 4,323,551 | 4/1982 | Parran | 424/54 |
| 4,657,758 | 4/1987 | Goldemberg et al. | 424/49 |
| 4,666,708 | 5/1987 | Goldemberg et al. | 424/49 |
| 4,772,461 | 9/1988 | Parran et al. | 424/52 |
| 4,950,479 | 8/1990 | Hill et al. | 424/49 |
| 4,980,153 | 12/1990 | Jackson et al. | 424/52 |
| 5,043,183 | 8/1991 | Gershon et al. | 424/52 |
| 5,229,103 | 7/1993 | Eagle et al. | 424/49 |

Primary Examiner—Shep K. Rose
Attorney, Agent, or Firm—Peter C. Richardson; Paul H. Ginsburg; Gezina Holtrust

[57] ABSTRACT

A stable liquid oral prebrushing composition for loosening and removing plaque present on dental surfaces has a pH of about 7.2 to about 7.9 and comprises dialkali metal pyrophosphate salts, tetraalkali metal pyrophosphate salts or mixtures thereof, together with sodium lauryl sulfate in amounts effective for removal of plaque when the composition is applied to dental surfaces.

23 Claims, No Drawings

PREBRUSHING PYROPHOSPHATE-CONTAINING LIQUID ORAL COMPOSITIONS

CROSS REFERENCE TO RELATED APPLICATIONS

This application is a continuation-in-part of application Ser. No. 896,275, filed Jun. 10, 1992, now abandoned, which in turn is a continuation-in-part of application Ser. No. 736,851 filed Jul. 29, 1991, now abandoned.

BACKGROUND OF THE INVENTION

The invention is concerned with liquid oral prebrushing compositions containing pyrophosphates and sodium lauryl sulfate for removal of plaque before brushing with a dentifrice.

Dental plaque is present to some degree, in the form of a film, on virtually all dental surfaces. It is a by-product of microbial growth, and comprises a dense microbial layer consisting of a mass of microorganisms embedded in a polysaccharide matrix. The microorganisms present in plaque are mainly coccoidal organisms, particularly in early plaque, which, in the mouths of some persons at least, change to filamentous organisms after a few days. Plaque itself adheres firmly to dental surfaces and is removed only with difficulty even through a rigorous brushing regimen. Moreover, plaque rapidly reforms on the tooth surface after it is removed.

Plaque may form on any part of the tooth surfaces, and is found particularly at the gingival margin, in pits and fissures in the enamel, and on the surface of dental calculus. As discussed in greater detail below, the danger associated with the formation of plaque on the teeth lies in the tendency of plaque to build up and eventually contribute to gingivitis, periodontitis and other types of periodontal disease, as well as dental caries and dental calculus.

More specifically, dental plaque is a precursor to the formation of the hard crystalline buildup on teeth referred to as dental calculus. Both the bacterial and the nonbacterial components of plaque mineralize to form calculus, which comprises mineralized bacteria as well as organic constituents, such as epithelial cells, live bacteria, salivary proteins, leucocytes, and crystals of substances having molecularly bound calcium and phosphorus, e.g., hydroxyapatite, $3[Ca_3(PO_4)_2]Ca(OH)_2$, octacalcium phosphate, $Ca_8(HPO_4)_2(PO_4)_4 5H_2O$, brushite, $CaHPO_4 2H_2O$, and whitlockite, which is considered to have the formula beta-$Ca_3(PO_4)_2$. Dental plaque and, hence, calculus are particularly prone to form at the gingival margin, i.e., the junction of the tooth and gingiva. The buildup of plaque at the gingival margin is believed to be the prime cause of gingivitis and other periodontal disorders.

Regular tooth brushing with a conventional dentifrice for some persons greatly retards or even prevents the accumulation of significant amounts of plaque and calculus. For other persons, however, plaque builds up rapidly even with regular brushing, which, in turn, leads to the formation of calculus, caries, and presents the danger of periodontal diseases. It is widely recognized in dentistry that a rigorous brushing regimen alone for many individuals will not prevent the formation of significant amounts of plaque.

Mouthwashes are employed in conventional regimens of oral hygiene. Conventional mouthwashes serve primarily to sweeten the breath, are formulated for that purpose, and are believed not to function in any significant way to loosen or remove plaque from the dental surfaces. Since the user typically does not employ a conventional mouthwash expressly for the purpose of cleansing the teeth of plaque, mouthwashes are not routinely used immediately prior to brushing as a way of rendering plaque more amenable to removal during the subsequent brushing process. The present prebrushing compositions of the invention instead are used immediately before brushing.

Liquid oral compositions, such as mouthrinses and mouthwashes, containing sodium lauryl sulfate as a surface active agent are known, e.g. as described in U.S. Pat. No. 4,666,708 which is incorporated herein by reference.

Pyrophosphate salts have been used for their anticalculus properties in toothpastes and mouthwashes according to U.S. Pat. Nos. 4,590,066 and 4,684,518.

SUMMARY OF THE INVENTION

The present invention relates to a liquid oral prebrushing composition for loosening and removing plaque present on dental surfaces comprising a detergent builder selected from the group consisting of a dialkali metal pyrophosphate salt, a tetraalkali metal pyrophosphate salt and a mixture thereof, and sodium lauryl sulfate in amounts effective for removal of plaque when said composition is applied to dental surfaces.

The invention also relates to a method for loosening and removing plaque present on dental surfaces by rinsing said dental surfaces with a liquid oral prebrushing composition comprising a detergent builder selected from the group consisting of a dialkali metal pyrophosphate salt, a tetraalkali metal pyrophosphate salt and a mixture thereof, and sodium lauryl sulfate in amounts effective for removal of plaque when said composition is applied to dental surfaces, said method further comprising the step of brushing said dental surfaces to which said prebrushing composition has been previously applied.

DETAILED DESCRIPTION OF THE INVENTION

The pyrophosphate salts useful in the present invention are dialkali metal pyrophosphate salts, tetraalkali metal pyrophosphate salts and mixtures thereof. Disodium pyrophosphate ($Na_2H_2P_2O_7$) and tetrasodium pyrophosphate are the preferred salts. The pyrophosphate salt is present in an amount which is effective in the removal of plaque when the prebrushing composition is applied to dental surfaces and the dental surfaces are then brushed.

The minimum amount of $P_2O_7^{-4}$ which is generally required is about 0.3% by weight. The maximum amount of $P_2O_7^{-4}$ depends on the solubility of the pyrophosphate salts in the rinse. In general, the maximum amount of $P_2O_7^{-4}$ is about 2.5% by weight.

The pyrophosphate salts of use in the invention are described in more detail in Kirk & Othmer, Encyclopedia of Chemical Technology, Third Edition, Volume 17, pages 454 to 456, Interscience Publishers (1982), incorporated herein by reference.

The sodium lauryl sulfate of use in the present invention is commercially available in different grades.

The sodium lauryl sulfate is present in an amount effective for the removal of plaque when the prebrushing composition of the invention is first applied to dental surfaces and the dental surfaces are then brushed. The amount of sodium lauryl sulfate will generally range from about 0.08 to about 2.0%, preferably about 0.08 to about 0.6%, by weight of the prebrushing composition.

The liquid carrier of the prebrushing composition of the invention generally includes water and ethanol. The amount of water preferably ranges from about 50% to about 85% by weight based on the weight of the prebrushing composition. The amount of ethanol preferably ranges from about 5% to about 25% by weight of the prebrushing composition.

The prebrushing composition of the invention has an alkaline pH ranging from about 7.2 to about 7.9, preferably about 7.7. At this pH, the composition is stable at low temperatures of about 35° F. The alkaline pH is obtained by a proper balancing of the type and amount of pyrophosphates or by addition of an alkaline or acidic agent. For instance, benzoic acid may be used to lower the pH, usually in combination with sodium benzoate. When this combination is used, the benzoate anion concentration is generally at a maximum of about 1.5% by weight of the composition, and usually about 1.0% by weight.

The stability of the composition according to the invention at low temperatures of about 35° F. is determined by cooling the composition to 35° F. and then evaluating it after storing for seven days for the absence of any precipitate or for the formation of precipitate, such as crystals or flocculated material, which redissolves on increasing the temperature of the composition to room temperature, The prebrushing composition of the invention may include a humectant to give a moist feel to the mouth. Certain humectants can also impart sweetness to the prebrushing composition. The humectant generally is present in an amount ranging from about 5 to 25% by weight of the prebrushing composition. Suitable humectants include edible polyhydric alcohols such as glycerol, sorbitol, and propylene glycol.

The prebrushing composition of the invention may in addition include ingredients effective to provide flavoring and coloring. The flavorant may be a flavoring oil such as oil of peppermint, spearmint, wintergreen, eucalyptus, lemon, and orange, and sweetening agents such as sucrose, lactose, maltose, saccharine, sodium cyclamate, etc. The amount of flavoring or sweetening agent generally ranges from about 0.002% to about 0.3% of the prebrushing composition.

The liquid oral prebrushing composition of the invention is prepared by mixing the ingredients. The prebrushing composition is used in a conventional manner by applying a comfortable amount, such as one tablespoon, in the mouth, and rinsing it about the dental surfaces. A reduction of the amount of plaque on dental surfaces is accomplished when the prebrushing composition of the invention is employed in conjunction with a conventional tooth brushing regimen.

The manner of making the prebrushing composition of the invention is illustrated by the following examples.

EXAMPLE 1

The following prebrushing composition was formulated:

| Components | % w/w |
| --- | --- |
| Purified Water | 75.6719 |
| Glycerin | 14.0000 |
| Alcohol | 7.0000 |
| Tetrasodium Pyrophosphate | 1.5600 |
| Sodium Benzoate | 0.3700 |
| Sodium Lauryl Sulfate | 0.4000 |
| Benzoic Acid | 0.5300 |
| Flavor solubilizer | 0.3000 |
| Flavor | 0.1200 |
| Xanthan Gum | 0.0300 |
| Sweetener | 0.0100 |
| Artificial Candied Sugar | 0.0075 |
| FD&C Blue #1 | 0.0004 |
| FD&C Yellow #5 | 0.0002 |
| | 100.0000% |

The pH of the prebrushing composition was 7.7.

Xanthan gum was slowly sprinkled into water having a temperature of 25° C. with mixing for about 30 minutes until complete dispersion. Tetrasodium pyrophosphate and benzoic acid were added with mixing for about 30 minutes until a uniform mixture was obtained.

The following ingredients were added in the following order while mixing at low speed for about 30 minutes until the solution was uniform:

Flavor Solubilizer
Sodium Lauryl Sulfate
Sodium benzoate
Glycerin
Sweetener
Artificial Candied Sugar
FD & C Blue #1
FD & C Yellow #5

The formulation amount of alcohol was mixed with the flavor until the mixture was uniform. This mixture was added to the above batch and the entire batch was mixed for about 30 minutes.

On reducing the temperature of the above clear formulation to 35° F., flocculation occurred on the fourth day and persisted during storing for seven days at 35° F. No crystals formed. The flocculation dissolved on increasing the temperature of the formulation to room temperature.

EXAMPLE 2

The following prebrushing composition was formulated in accordance with the procedure of Example 1:

| Components | % w/w |
| --- | --- |
| Purified Water | 75.6178 |
| Glycerin | 14.0000 |
| Alcohol | 7.0000 |
| Tetrasodium Pyrophosphate | 1.5600 |
| Sodium Benzoate | 0.3700 |
| Sodium Lauryl Sulfate | 0.4000 |
| Benzoic Acid | 0.5300 |
| Flavor solubilizer | 0.3000 |
| Flavor | 0.1800 |
| Xanthan Gum | 0.0300 |
| FD&C Red #40 | 0.0080 |
| Sweetener | 0.0042 |
| | 100.0000% |

The pH of the prebrushing composition was 7.7.

On reducing the temperature of the above clear formulation to 35° F., flocculation occurred on the first day and persisted during storing for seven days at 35° F.

No crystals formed. The flocculation dissolved on increasing the temperature of the formulation to room temperature.

We claim:

1. A stable, liquid oral prebrushing composition for loosening and removing plaque present on dental surfaces which composition is free from flocculation or crystal formation after storing for seven days at about 35 °F. or redissolves any flocculation or crystal formation at about 35° F. on increasing the temperature of the composition to room temperature comprising a detergent builder selected from the group consisting of a dialkali metal pyrophosphate salt, a tetraalkali metal pyrophosphate salt and a mixture thereof providing at least about 0.3% by weight $P_2O_7^{-4}$, and about 0.08 to about 2.0% by weight of sodium lauryl sulfate based on the weight of the prebrushing composition, said composition having a pH of about 7.2 to about 7.9.

2. A composition according to claim 1 wherein said composition has a pH of about 7.7.

3. A composition according to claim 1 comprising about 50% to about 85% by weight of water based on the weight of the prebrushing composition.

4. A composition according to claim 1 comprising about 5% to about 25% by weight of ethanol based on the weight of the prebrushing composition.

5. A composition according to claim 1 comprising in percentages by weight based on the weight of the prebrushing composition
   (a) 0.3 to 2.5% by weight of $P_2O_7^{-4}$,
   (b) 0.08 to 0.6% by weight of sodium lauryl sulfate,
   (c) 50 to 85% by weight of water, and
   (d) 5 to 25% by weight of ethanol.

6. A composition according to claim 1 wherein said composition includes a humectant.

7. A composition according to claim 6 wherein about 5 to 25% by weight of glycerine is included.

8. A method for loosening and removing plaque present on dental surfaces which composition is free from flocculation or crystal formation after storing for seven days at about 35° F. or redissolves any flocculation or crystal formation at about 35° F. on increasing the temperature of the composition to room temperature comprising rinsing said dental surfaces with a liquid oral prebrushing composition, wherein said prebrushing composition comprises a detergent builder selected from the group consisting of a dialkali metal pyrophosphate sale, a tetraalkali metal pyrophosphate salt and a mixture thereof providing at least about 0.3% by weight $P_2O_7^{-4}$, and about 0.08 to about 2.0% by weight of sodium lauryl sulfate based on the weight of the prebrushing composition, and said method further comprising the step of brushing the dental surfaces to which said prebrushing composition has been previously applied.

9. A method according to claim 8 wherein said composition has a pH of about 7.2 to amount 7.9.

10. A method according to claim 8 wherein said composition has a pH of about 7.7.

11. A method according to claim 8 wherein said prebrushing comprises about 50% to about 85% by weight of water based on the weight of the prebrushing composition.

12. A method according to claim 8 wherein said prebrushing comprises about 50% to about 85% by weight of ethanol based on the weight of the prebrushing composition.

13. A method according to claim 8 wherein said prebrushing comprises in percentages by weight based on the weight of the prebrushing composition
   (a) 0.3 to 2.5% by weight of $P_2O_7^{-4}$,
   (b) 0.08 to 0.6% by weight of sodium lauryl sulfate,
   (c) 50 to 85% by weight of water, and
   (d) 5 to 25% by weight of ethanol.

14. A method according to claim 8 wherein said prebrushing composition includes a humectant.

15. A method according to claim 14 wherein about 5 to 25% by weight of glycerine is included in said prebrushing composition.

16. A stable, liquid oral prebrushing composition for loosening and removing plaque present on dental surfaces which composition is free from flocculation or crystal formation after storing for seven days at about 35° F. or redissolves any flocculation or crystal formation at about 35° F. on increasing the temperature of the composition to room temperature consisting essentially of a detergent builder selected from the group consisting of a dialkali metal pyrophosphate sale, a tetraalkali metal pyrophosphate salt and a mixture thereof providing at least about 0.3% by weight $P_2O_7^{-4}$, and about 0.08 to about 2.0% by weight of sodium lauryl sulfate based on the weight of the prebrushing composition, said composition having a pH of about 7.2 to about 7.9.

17. A composition according to claim 16 wherein said composition has a pH of about 7.7.

18. A composition according to claim 16 comprising about 50% to about 85% by weight of water based on the weight of the prebrushing composition.

19. A composition according to claim 16 comprising about 5% to about 25% by weight of ethanol based on the weight of the prebrushing composition.

20. A composition according to claim 16 comprising in percentages by weight based on the weight of the prebrushing composition
   (a) 0.3 to 2.5% by weight of $P_2O_7^{-4}$,
   (b) 0.08 to 2.0% by weight of sodium lauryl sulfate,
   (c) 50 to 85% by weight of water, and
   (d) 5 to 25% by weight of ethanol.

21. A composition according to claim 16 wherein said composition includes a humectant.

22. A composition according to claim 21 wherein about 5 to 25% by weight of glycerine is included.

23. A stable, liquid oral prebrushing composition for loosening and removing plaque present on dental surfaces which composition is free from flocculation or crystal formation after storing for seven days at about 35° F. or redissolves any flocculation or crystal formation at about 35° F. on increasing the temperature of the composition to room temperature essentially consisting of a detergent builder selected from the group consisting of a dialkali metal pyrophosphate salt, a tetraalkali metal pyrophosphate salt and a mixture thereof providing at least about 0.3% by weight $P_2O_7^{-4}$, and about 0.08 to about 2.0% by weight of sodium lauryl sulfate based on the weight of the prebrushing composition, about 50% to about 85% by weight of water based on the weight of the prebrushing composition, about 5% to about 25% by weight of each of ethanol and glycerine based on the weight of the prebrushing composition, humectant, sodium benzoate, benzoic acid, a flavor, a flavor solubilizer, xanthan gum, sweetener and coloring, said composition having a pH of about 7.2 to about 7.9.

* * * * *